US010762442B2

(12) United States Patent
Singer

(10) Patent No.: US 10,762,442 B2
(45) Date of Patent: *Sep. 1, 2020

(54) MACHINE LEARNING SYSTEM FOR ASSESSING HEART VALVES AND SURROUNDING CARDIOVASCULAR TRACTS

(71) Applicant: Stenomics, Inc., Belmont, CA (US)

(72) Inventor: Michael A. Singer, Belmont, CA (US)

(73) Assignee: Stenomics, Inc., Belmont, CA (US)

( * ) Notice: Subject to any disclaimer, the term of this patent is extended or adjusted under 35 U.S.C. 154(b) by 607 days.

This patent is subject to a terminal disclaimer.

(21) Appl. No.: 15/588,317

(22) Filed: May 5, 2017

(65) Prior Publication Data
US 2017/0337488 A1 Nov. 23, 2017

Related U.S. Application Data

(63) Continuation of application No. 15/138,922, filed on Apr. 26, 2016, now Pat. No. 9,953,272, which is a
(Continued)

(51) Int. Cl.
*G06N 20/00* (2019.01)
*A61B 5/00* (2006.01)
(Continued)

(52) U.S. Cl.
CPC .......... *G06N 20/00* (2019.01); *A61B 5/7253* (2013.01); *A61B 5/7267* (2013.01);
(Continued)

(58) Field of Classification Search
USPC ........................................................ 706/12
See application file for complete search history.

(56) References Cited

U.S. PATENT DOCUMENTS 5,533,511 A    7/1996    Kaspari et al.
6,304,848 B1 *  10/2001   Singer .................. G06Q 10/10
                                                                705/3
(Continued)

FOREIGN PATENT DOCUMENTS

JP     2007-526016 A    9/2007
JP     2012024582 A     2/2012
(Continued)

OTHER PUBLICATIONS

Auricchio et al., "Simulation of transcatheter aortic valve implanatation: a patient-specific finite element approach," Computer Methods in Biomechanics and Biomedical Engineering, 2013, pp. 1-11.
(Continued)

*Primary Examiner* — Michael B Holmes
(74) *Attorney, Agent, or Firm* — Chernoff, Vilhauer, McClung & Stenzel, LLP

(57) ABSTRACT

A machine learning system for evaluating at least one characteristic of a heart valve, an inflow tract, an outflow tract or a combination thereof may include a training mode and a production mode. The training mode may be configured to train a computer and construct a transformation function to predict an unknown anatomical characteristic and/or an unknown physiological characteristic of a heart valve, inflow tract and/or outflow tract, using a known anatomical characteristic and/or a known physiological characteristic the heart valve, inflow tract and/or outflow tract. The production mode may be configured to use the transformation function to predict the unknown anatomical characteristic and/or the unknown physiological characteristic of the heart valve, inflow tract and/or outflow tract, based on the known anatomical characteristic and/or the known physiological characteristic of the heart valve, inflow tract and/or outflow tract.

55 Claims, 7 Drawing Sheets

Related U.S. Application Data continuation of application No. 14/680,892, filed on Apr. 7, 2015, now Pat. No. 9,424,531, which is a continuation of application No. 14/511,018, filed on Oct. 9, 2014, now Pat. No. 9,092,743.

(60) Provisional application No. 61/894,814, filed on Oct. 23, 2013.

(51) Int. Cl.

| | | |
|---|---|---|
| *G06N 5/04* | (2006.01) | |
| *A61B 34/10* | (2016.01) | |
| *G16H 50/50* | (2018.01) | |
| *G16H 50/20* | (2018.01) | |
| *G06F 17/11* | (2006.01) | |
| *G06F 19/00* | (2018.01) | |

(52) U.S. Cl.
CPC ............ *A61B 5/7275* (2013.01); *A61B 34/10* (2016.02); *G06F 17/11* (2013.01); *G06F 19/00* (2013.01); *G06N 5/04* (2013.01); *G16H 50/20* (2018.01); *G16H 50/50* (2018.01)

(56) References Cited

U.S. PATENT DOCUMENTS

| | | | |
|---|---|---|---|
| 6,377,832 B1 | 4/2002 | Bergman et al. | |
| 6,587,830 B2 * | 7/2003 | Singer | G06Q 10/10 705/3 |
| 8,098,918 B2 | 1/2012 | Zheng et al. | |
| 8,157,742 B2 | 4/2012 | Taylor | |
| 8,219,229 B2 | 7/2012 | Cao et al. | |
| 8,224,640 B2 | 7/2012 | Sharma et al. | |
| 8,249,815 B2 | 8/2012 | Taylor | |
| 8,311,747 B2 | 11/2012 | Taylor | |
| 8,311,748 B2 | 11/2012 | Taylor et al. | |
| 8,311,750 B2 | 11/2012 | Taylor | |
| 8,315,812 B2 | 11/2012 | Taylor | |
| 8,315,813 B2 | 11/2012 | Taylor et al. | |
| 8,315,814 B2 | 11/2012 | Taylor | |
| 8,321,150 B2 | 11/2012 | Taylor | |
| 8,386,188 B2 | 2/2013 | Taylor et al. | |
| 8,496,594 B2 | 7/2013 | Taylor et al. | |
| 8,523,779 B2 | 9/2013 | Taylor et al. | |
| 8,548,778 B1 | 10/2013 | Hart et al. | |
| 8,560,057 B2 | 10/2013 | Lundback | |
| 8,606,530 B2 | 12/2013 | Taylor | |
| 8,630,812 B2 | 1/2014 | Taylor | |
| 8,647,381 B2 | 2/2014 | Essinger et al. | |
| 8,682,626 B2 | 3/2014 | Ionasec et al. | |
| 8,684,921 B2 | 4/2014 | Osorio | |
| 8,706,457 B2 | 4/2014 | Hart et al. | |
| 8,734,356 B2 | 5/2014 | Taylor | |
| 8,734,357 B2 | 5/2014 | Taylor | |
| 8,768,669 B1 | 7/2014 | Hart et al. | |
| 8,768,670 B1 | 7/2014 | Hart et al. | |
| 8,812,245 B2 | 8/2014 | Taylor | |
| 8,812,246 B2 | 8/2014 | Taylor | |
| 8,821,408 B2 | 9/2014 | Hu et al. | |
| 8,824,752 B1 | 9/2014 | Fonte et al. | |
| 8,831,314 B1 | 9/2014 | Fonte et al. | |
| 8,831,315 B1 | 9/2014 | Fonte et al. | |
| 8,837,860 B1 | 9/2014 | Grady et al. | |
| 8,855,984 B2 | 10/2014 | Hart et al. | |
| 8,861,820 B2 | 10/2014 | Fonte et al. | |
| 8,914,264 B1 | 12/2014 | Hart et al. | |
| 8,917,925 B1 | 12/2014 | Grady et al. | |
| 8,958,623 B1 | 2/2015 | Grady et al. | |
| 9,002,690 B2 | 4/2015 | Hart et al. | |
| 9,008,392 B1 | 4/2015 | Bai et al. | |
| 9,008,405 B2 | 4/2015 | Fonte et al. | |
| 9,042,613 B2 | 5/2015 | Spilker et al. | |
| 9,043,190 B2 | 5/2015 | Grady et al. | |
| 9,043,191 B2 | 5/2015 | Grady et al. | |
| 9,058,692 B1 | 6/2015 | Grady et al. | |
| 9,063,634 B2 | 6/2015 | Hart et al. | |
| 9,063,635 B2 | 6/2015 | Hart et al. | |
| 9,070,214 B1 | 6/2015 | Grady et al. | |
| 9,078,564 B2 | 7/2015 | Taylor | |
| 9,081,721 B1 | 7/2015 | Grady et al. | |
| 9,081,882 B2 | 7/2015 | Taylor | |
| 9,087,147 B1 | 7/2015 | Fonte | |
| 9,092,743 B2 * | 7/2015 | Singer | A61B 5/7275 |
| 9,135,381 B2 * | 9/2015 | Singer | G06F 30/23 |
| 9,149,197 B2 | 10/2015 | Taylor | |
| 9,152,757 B2 | 10/2015 | Taylor | |
| 9,152,761 B2 | 10/2015 | Bhatia et al. | |
| 9,153,047 B1 | 10/2015 | Grady et al. | |
| 9,155,512 B2 | 10/2015 | Choi et al. | |
| 9,159,159 B2 | 10/2015 | Bai et al. | |
| 9,167,974 B2 | 10/2015 | Taylor | |
| 9,168,012 B2 | 10/2015 | Hart et al. | |
| 9,189,600 B2 | 11/2015 | Spilker et al. | |
| 9,195,800 B2 | 11/2015 | Grady et al. | |
| 9,195,801 B2 | 11/2015 | Sankaran et al. | |
| 9,202,010 B2 | 12/2015 | Taylor et al. | |
| 9,220,418 B2 | 12/2015 | Choi et al. | |
| 9,220,419 B2 | 12/2015 | Choi et al. | |
| 9,226,672 B2 | 1/2016 | Taylor | |
| 9,235,679 B2 | 1/2016 | Taylor | |
| 9,239,905 B1 | 1/2016 | Sankaran et al. | |
| 9,262,581 B2 | 2/2016 | Kim et al. | |
| 9,268,902 B2 | 2/2016 | Taylor et al. | |
| 9,271,657 B2 | 3/2016 | Taylor | |
| 9,280,639 B2 | 3/2016 | Sankaran et al. | |
| 9,292,659 B1 | 3/2016 | Grady et al. | |
| 9,304,982 B2 | 4/2016 | Grady et al. | |
| 9,330,233 B2 | 5/2016 | Bhatia et al. | |
| 9,336,354 B1 | 5/2016 | Sankaran et al. | |
| 9,339,200 B2 | 5/2016 | Fonte | |
| 9,349,178 B1 | 5/2016 | Itu et al. | |
| 9,378,580 B2 | 6/2016 | Grady et al. | |
| 9,386,933 B2 | 7/2016 | Grady et al. | |
| 9,390,224 B2 | 7/2016 | Choi et al. | |
| 9,390,232 B2 | 7/2016 | Taylor et al. | |
| 9,424,395 B2 | 8/2016 | Sankaran et al. | |
| 9,424,531 B2 * | 8/2016 | Singer | A61B 5/7275 |
| 9,424,682 B2 | 8/2016 | Bai et al. | |
| 9,449,145 B2 | 9/2016 | Sankaran et al. | |
| 9,449,146 B2 | 9/2016 | Spilker et al. | |
| 9,449,147 B2 | 9/2016 | Taylor | |
| 9,501,622 B2 | 11/2016 | Sankaran et al. | |
| 9,514,530 B2 | 12/2016 | Grady et al. | |
| 9,517,040 B2 | 12/2016 | Hart et al. | |
| 9,585,623 B2 | 3/2017 | Fonte et al. | |
| 9,585,723 B2 | 3/2017 | Taylor | |
| 9,589,349 B2 | 3/2017 | Grady et al. | |
| 9,594,876 B2 | 3/2017 | Sankaran et al. | |
| 9,607,130 B2 | 3/2017 | Grady et al. | |
| 9,607,386 B2 | 3/2017 | Grady et al. | |
| 9,613,186 B2 | 4/2017 | Fonte | |
| 9,630,324 B2 * | 4/2017 | Cohen | B25J 9/1661 |
| 9,649,171 B2 | 5/2017 | Sankaran et al. | |
| 9,668,700 B2 | 6/2017 | Taylor | |
| 9,672,615 B2 | 6/2017 | Fonte et al. | |
| 9,675,301 B2 | 6/2017 | Fonte et al. | |
| 9,679,374 B2 | 6/2017 | Choi et al. | |
| 9,697,330 B2 | 7/2017 | Taylor | |
| 9,706,925 B2 | 7/2017 | Taylor | |
| 9,743,835 B2 | 8/2017 | Taylor | |
| 9,754,082 B2 | 9/2017 | Taylor et al. | |
| 9,770,303 B2 | 9/2017 | Choi et al. | |
| 9,773,219 B2 | 9/2017 | Sankaran et al. | |
| 9,785,746 B2 | 10/2017 | Fonte et al. | |
| 9,785,748 B2 | 10/2017 | Koo et al. | |
| 9,801,689 B2 | 10/2017 | Taylor | |
| 9,805,168 B2 | 10/2017 | Sankaran et al. | |
| 9,805,463 B2 | 10/2017 | Choi et al. | |
| 9,805,470 B2 | 10/2017 | Bhatia | |
| 9,953,272 B2 * | 4/2018 | Singer | A61B 5/7267 |
| 10,497,476 B2 * | 12/2019 | Singer | G06F 30/23 |
| 2002/0087357 A1 | 7/2002 | Singer | |
| 2003/0004652 A1 | 1/2003 | Brunner | |

(56) References Cited

U.S. PATENT DOCUMENTS

| | | |
|---|---|---|
| 2003/0087244 A1 | 5/2003 | McCarthy |
| 2003/0195409 A1 | 10/2003 | Seitz et al. |
| 2004/0153128 A1 | 8/2004 | Suresh et al. |
| 2005/0049497 A1 | 3/2005 | Krishnan et al. |
| 2008/0292049 A1 | 11/2008 | Camus et al. |
| 2008/0319308 A1 | 12/2008 | Tang |
| 2009/0080745 A1 | 3/2009 | Zheng et al. |
| 2009/0103794 A1 | 4/2009 | Sathyanarayana |
| 2010/0130878 A1 | 5/2010 | Lasso et al. |
| 2011/0060576 A1 | 3/2011 | Sharma et al. |
| 2011/0071404 A1 | 3/2011 | Schmitt et al. |
| 2012/0022843 A1 | 1/2012 | Ionasec et al. |
| 2012/0041318 A1 | 2/2012 | Taylor |
| 2012/0041739 A1 | 2/2012 | Taylor |
| 2012/0053918 A1 | 3/2012 | Taylor et al. |
| 2012/0083699 A1 | 4/2012 | Reuter et al. |
| 2012/0201446 A1 | 8/2012 | Yang |
| 2012/0232386 A1 | 9/2012 | Mansi et al. |
| 2012/0232853 A1 | 9/2012 | Voigt et al. |
| 2013/0197884 A1 | 8/2013 | Mansi et al. |
| 2013/0243294 A1 | 9/2013 | Ralovich et al. |
| 2013/0246034 A1 | 9/2013 | Sharma |
| 2014/0046642 A1 | 2/2014 | Hart et al. |
| 2014/0073976 A1 | 3/2014 | Fonte et al. |
| 2014/0073977 A1 | 3/2014 | Grady et al. |
| 2014/0107935 A1 | 4/2014 | Taylor |
| 2014/0114184 A1 | 4/2014 | Klaiman et al. |
| 2014/0249790 A1 | 4/2014 | Spilker et al. |
| 2014/0148693 A1 | 5/2014 | Taylor |
| 2014/0155770 A1 | 6/2014 | Taylor |
| 2014/0164969 A1 | 6/2014 | Hart et al. |
| 2014/0173486 A1 | 6/2014 | Hart et al. |
| 2014/0207432 A1 | 7/2014 | Taylor |
| 2014/0222406 A1 | 8/2014 | Taylor |
| 2014/0236492 A1 | 8/2014 | Taylor |
| 2014/0236553 A1 | 8/2014 | Hart et al. |
| 2014/0243663 A1 | 8/2014 | Taylor |
| 2014/0247970 A1 | 9/2014 | Taylor |
| 2014/0249784 A1 | 9/2014 | Sankaran et al. |
| 2014/0249791 A1 | 9/2014 | Taylor |
| 2014/0249792 A1 | 9/2014 | Taylor |
| 2014/0270427 A1 | 9/2014 | Fonte et al. |
| 2014/0275945 A1 | 9/2014 | Fonte et al. |
| 2014/0275946 A1 | 9/2014 | Fonte et al. |
| 2014/0275947 A1 | 9/2014 | Fonte et al. |
| 2014/0292752 A1 | 10/2014 | Hart et al. |
| 2014/0303495 A1 | 10/2014 | Fonte et al. |
| 2014/0303510 A1 | 10/2014 | Fonte et al. |
| 2014/0336995 A1 | 11/2014 | Singer |
| 2015/0042646 A1 | 2/2015 | Comaniciu et al. |
| 2015/0051884 A1 | 2/2015 | Grady et al. |
| 2015/0051885 A1 | 2/2015 | Grady et al. |
| 2015/0051886 A1 | 2/2015 | Grady et al. |
| 2015/0066818 A1 | 3/2015 | Choi et al. |
| 2015/0112182 A1 | 4/2015 | Sharma et al. |
| 2015/0112901 A1 | 4/2015 | Singer |
| 2015/0164451 A1 | 6/2015 | Choi et al. |
| 2015/0164452 A1 | 6/2015 | Choi et al. |
| 2015/0164453 A1 | 6/2015 | Choi et al. |
| 2015/0202019 A1 | 7/2015 | Singer |
| 2015/0245775 A1 | 9/2015 | Fonte et al. |
| 2015/0273693 A1 | 10/2015 | Cohen |
| 2015/0278727 A1 | 10/2015 | Sankaran et al. |
| 2015/0278976 A1 | 10/2015 | Sankaran et al. |
| 2015/0282765 A1 | 10/2015 | Goshen et al. |
| 2015/0302578 A1 | 10/2015 | Grady et al. |
| 2015/0379231 A1 | 12/2015 | Singer |
| 2016/0110517 A1 | 4/2016 | Taylor |
| 2016/0110866 A1 | 4/2016 | Taylor |
| 2016/0110867 A1 | 4/2016 | Taylor |
| 2016/0113528 A1 | 4/2016 | Taylor |
| 2016/0113726 A1 | 4/2016 | Taylor |
| 2016/0117815 A1 | 4/2016 | Taylor |
| 2016/0117816 A1 | 4/2016 | Taylor |
| 2016/0117819 A1 | 4/2016 | Taylor |
| 2016/0128661 A1 | 5/2016 | Taylor |
| 2016/0133015 A1 | 5/2016 | Taylor |
| 2016/0140313 A1 | 5/2016 | Taylor |
| 2016/0148371 A1 | 5/2016 | Itu et al. |
| 2016/0148372 A1 | 5/2016 | Itu et al. |
| 2016/0166209 A1 | 6/2016 | Itu et al. |
| 2016/0232667 A1 | 8/2016 | Taylor |
| 2016/0246939 A1 | 8/2016 | Taylor |
| 2016/0310018 A1 | 10/2016 | Fonte et al. |
| 2016/0310019 A1 | 10/2016 | Fonte et al. |
| 2016/0310096 A1 | 10/2016 | Fonte et al. |
| 2016/0317046 A1 | 11/2016 | Fonte et al. |
| 2016/0317114 A1 | 11/2016 | Fonte et al. |
| 2016/0321417 A1 | 11/2016 | Fonte et al. |
| 2016/0364859 A1 | 12/2016 | Taylor |
| 2016/0364860 A1 | 12/2016 | Taylor |
| 2016/0364861 A1 | 12/2016 | Taylor |
| 2016/0371455 A1 | 12/2016 | Taylor |
| 2017/0095292 A1 | 4/2017 | Taylor et al. |
| 2017/0265831 A1 | 9/2017 | Sankaran et al. |
| 2017/0281011 A1 | 10/2017 | Fonte et al. |
| 2017/0337488 A1 | 11/2017 | Singer |

FOREIGN PATENT DOCUMENTS

| | | |
|---|---|---|
| JP | 2012159990 A | 8/2012 |
| JP | 2013-534154 A | 9/2013 |
| JP | 2015-527901 A | 9/2015 |
| WO | 2005001769 | 1/2005 |
| WO | 2011015822 A1 | 2/2011 |

OTHER PUBLICATIONS

Bernhard et al., "Transient Integral Boundary Layer Method to Calculate the Translesional Pressure Drop and the Fractional Flow Reserve in Myodcardial Bridges," Biomedical Engineering Online, Jun. 21, 20006, pp. 1-25, vol. 5, No. 42.

Bernstein et al., "Bicuspid-Valved PTFE Conduit Optimization for Pediatric RVOT Reconstruction," IEEE, 2011, 2 pgs.

Chalopin et al., "Automatic Labeling of the Coronary Tree Using a Three Dimensional Reference Prior Model," Computers in Cardiology, 1998, pp. 761-764, vol. 25.

Chandran, "Role of Computational Simulations in Heart Valve Dynamics and Design of Valvular Prostheses," Cardiovasc. Eng. Technol., Mar. 2010, pp. 1-30, vol. 1, No. 1.

Dumont et al., "Validation of a Fluid-Structure Interaction Model of a Heart Valve Using the Dynamic Mesh Method in Fluent," Computer Methods in Biomechanics and Biomedical Engineering, Jun. 2004, pp. 139-146, vol. 7, No. 3.

Enevoldsen et al., "Computational Fluid Dynamics Using In Vivo Ultrasound Blood Flow Measurements," Ultrasonics Symposium (IUS), 2012 IEEE International, Oct. 2012, 4 pgs.

FDA, The Integration of Nonclinical and Computer Models, National Science Foundation Workshop on Computer Methods in Cardiovascular Device Design and Evaluation, FDA / A / NSF / NHLB1 Workshop on Computer Methods for Cardiovascular Devices—The Integration of Nonclinical and Computer Models, Jun. 9-11, 2010, pp. 1-7.

Gaillard et al., "Optimization of Doppler Velocity Echocardiographic Measurements Using an Automatic Contour Detection Method," 31st Annual International Conference of the IEEE EMBS, Sep. 2-6, 2009, pp. 2264-2267.

Haj-Ali et al., "A general three-dimensional parametric geometry of the native aortic valve and root for biomechanical modeling," Journal of Biomechanics, 2012, pp. 2392-2397, vol. 45.

Le et al., "Fluid-structure interaction of a aortic heart valve prosthesis driven by an animated anatomic left ventricle," Journal of Computational Physics, Jul. 1, 2013, pp. 1-38, vol. 244.

Marom et a., "Numerical model of the aortic root and valve: Optimization of graft size and sinotubular junction to annulus ratio," The Journal of Thoracic and Cardiovascular Surgery, 2013, pp. 1-6.

Min et al., "An Edge-Based Prediction Approach for Medical Image Compression," IEEE EMBS International Conference on Biomedical Engineering and Sciences, Dec. 17-19, 2012, pp. 717-722.

(56) References Cited

OTHER PUBLICATIONS

Neal et al., "Current Progress in Patient-Specific Modeling," Briefings in Bioinformatics, Dec. 2, 2009, pp. 111-126, vol. 2, No. 1.
Shim et al., "Numerical Analysis of Blood Flow through a Stenosed Artery Using a Coupled Multiscale Simulation Method," Computers in Cardiology, 2000, pp. 219-222, vol. 27.
Tan et al., "Comparison of Aortic Flow Patterns Before and After Transcatheter Aortic Valve Implantation," Cardiovascular Engineering and Technology, Mar. 2012, pp. 123-135, vol. 3, No. 1.
Voigt et al., "Patient-Specific Model of Left Heart Anatomy, Dynamics and Hemodynamics from 4D TE: A First Validation Study," D.N. Metaxas and L. Axel (Eds.), 2011, pp. 341-349.
Votta et al., "Toward patient-specific simulations of cardiac valves: State-of-the-art and future directions," Journal of Biomechanics, 2013, pp. 217-228, vol. 46.
Wang et al., "Patient-specific modeling of biomechanical interaction in transcatheter aortic valve deployment," Journal of Biomechanics, 2012, p. 1965-1971, vol. 45.
Weinberg et al., "Transient, Three-dimensional, Multiscale Simulations of the Human Aortic Valve," Cardiovasc. Eng., 2007, 16 pgs.
Wendell, "Incorporating the Aortic Valve into Computational Fluid Dynamics Models using Phase-contrast MRI and Valve Tracking," Paper 170, http://epublications.maruette.edu/dissertations_mu/170., Dissertations, 2009-, 176 pgs., 4 parts.
Wissel et al., "Preliminary Study on Optical Feature Detection for Head Tracking in Radiation Therapy," IEEE, 2013, 5 pgs.
Yoganathan et al., "Flow in Prosthetic Heart Valves: State-of-the-Art and Future Directions," Annals of Biomedical Engineering, Dec. 2005, pp. 1689-1694, vol. 33, No. 12.
International Search Report, PCT International App. No. PCT/US2013/057546, dated Nov. 18, 2013, 4 pgs.
International Search Report, PCT International App. No. PCT/US2014/061898, dated Feb. 5, 2015, 2 pgs.
International Search Report and Written Opinion, PCT International App. No. PCT/US2014/035914, dated Aug. 26, 2014, 16 pgs.
Written Opinion of PCT International App. No. PCT/US2014/061898, dated Feb. 5, 2015, 10 pgs.
Extended European Search Report, dated Dec. 21, 2016, European Patent App. No. 14794544.8, 7 pgs.
File history of U.S. Appl. No. 13/625,628, filed Sep. 24, 2012, " Method and System for Facilitating Physiological Computations", 151 pgs.
File history of U.S. Appl. No. 13/895,871, filed May 16, 2013, "Systems and Methods for Estimating Ischemia and Blood Flow Characteristics from Vessel Geometry and Physiology", 619 pgs.
File history of U.S. Appl. No. 13/895,893, filed May 16, 2013, "Systems and Methods for Estimating Blood Flow Characteristics from Vessel Geometry and Physiology", 576 pgs.
File history of U.S. Appl. No. 14/716,046, filed May 19, 2015, "Systems and Methods for Estimating Ischemia and Blood Flow Characteristics from Vessel Geometry and Physiology", 548 pgs.
File history of U.S. Appl. No. 14/988,040, filed Jan. 5, 2016, "Method and System for Facilitating Physiological Computations", 153 pgs.
File history of U.S. Appl. No. 15/200,160, filed Jul. 1, 2016, "Systems and Methods for Estimating Ischemia and Blood Flow Characteristics from Vessel Geometry and Physiology", 449 pgs.
File history of U.S. Appl. No. 15/200,318, filed Jul. 1, 2016, "Systems and Methods for Estimating Ischemia and Blood Flow Characteristics from Vessel Geometry and Physiology", 376 pgs.
File history of U.S. Appl. No. 15/200,402, filed Jul. 1, 2016, "Systems and Methods for Estimating Ischemia and Blood Flow Characteristics from Vessel Geometry and Physiology", 119 pgs.
File history of U.S. Appl. No. 15/205,536, filed Jul. 8, 2016, "Systems and Methods for Estimating Ischemia and Blood Flow Characteristics from Vessel Geometry and Physiology", 410 pgs.
File history of U.S. Appl. No. 15/205,583, filed Jul. 8, 2016, "Systems and Methods for Estimating Ischemia and Blood Flow Characteristics from Vessel Geometry and Physiology", 417 pgs.
File history of U.S. Appl. No. 15/205,623, filed Jul. 8, 2016, "Systems and Methods for Estimating Ischemia and Blood Flow Characteristics from Vessel Geometry and Physiology", 416 pgs.
File history of U.S. Appl. No. 15/624,424, filed Jun. 15, 2017, "Systems and Methods of Image Processing to Determine Flow Characteristics", 301 pgs.
International Search Report and Written Opinion, dated Nov. 18, 2013, PCT International App. No. PCT/US2013/057546, Heartflow, Inc., 10 pgs.
International Preliminary Report on Patentability, dated Mar. 26, 2015, PCT International App. No. PCT/US2013/057546, Heartflow, Inc., 6 pgs.
Bernhard et al., "Transient integral boundary layer method to calculate the translesional pressure drop and the fractional flow reserve in myocardial bridges," Biomedical Engineering OnLine, Jun. 21, 2006, 29, pgs.
File history of U.S. Appl. No. 13/895,871, filed May 16, 2013, entitled Systems and Methods for Estimating Ischemia and Blood Flow Characteristics from Vessel Geometry and Physiology, Part 1, 50 pgs.
File history of U.S. Appl. No. 13/895,871, filed May 16, 2013, entitled Systems and Methods for Estimating Ischemia and Blood Flow Characteristics from Vessel Geometry and Physiology, Part 2, 50 pgs.
File history of U.S. Appl. No. 13/895,871, filed May 16, 2013, entitled Systems and Methods for Estimating Ischemia and Blood Flow Characteristics from Vessel Geometry and Physiology, Part 3, 50 pgs.
File history of U.S. Appl. No. 13/895,871, filed May 16, 2013, entitled Systems and Methods for Estimating Ischemia and Blood Flow Characteristics from Vessel Geometry and Physiology, Part 4, 50 pgs.
File history of U.S. Appl. No. 13/895,871, filed May 16, 2013, entitled Systems and Methods for Estimating Ischemia and Blood Flow Characteristics from Vessel Geometry and Physiology, Part 5, 50 pgs.
File history of U.S. Appl. No. 13/895,871, filed May 16, 2013, entitled Systems and Methods for Estimating Ischemia and Blood Flow Characteristics from Vessel Geometry and Physiology, Part 6, 50 pgs.
File history of U.S. Appl. No. 13/895,871, filed May 16, 2013, entitled Systems and Methods for Estimating Ischemia and Blood Flow Characteristics from Vessel Geometry and Physiology, Part 7, 50 pgs.
File history of U.S. Appl. No. 13/895,871, filed May 16, 2013, entitled Systems and Methods for Estimating Ischemia and Blood Flow Characteristics from Vessel Geometry and Physiology, Part 8, 50 pgs.
File history of U.S. Appl. No. 13/895,871, filed May 16, 2013, entitled Systems and Methods for Estimating Ischemia and Blood Flow Characteristics from Vessel Geometry and Physiology, Part 9, 50 pgs.
File history of U.S. Appl. No. 13/895,871, filed May 16, 2013, entitled Systems and Methods for Estimating Ischemia and Blood Flow Characteristics from Vessel Geometry and Physiology, Part 10, 50 pgs.
File history of U.S. Appl. No. 13/895,871, filed May 16, 2013, entitled Systems and Methods for Estimating Ischemia and Blood Flow Characteristics from Vessel Geometry and Physiology, Part 11, 50 pgs.
File history of U.S. Appl. No. 13/895,871, filed May 16, 2013, entitled Systems and Methods for Estimating Ischemia and Blood Flow Characteristics from Vessel Geometry and Physiology, Part 12, 38 pgs.
File history of U.S. Appl. No. 13/895,893, filed May 16, 2013, entitled Systems and Methods for Estimating Ischemia and Blood Flow Characteristics from Vessel Geometry and Physiology, Part 1, 50 pgs.
File history of U.S. Appl. No. 13/895,893, filed May 16, 2013, entitled Systems and Methods for Estimating Ischemia and Blood Flow Characteristics from Vessel Geometry and Physiology, Part 2, 50 pgs.

(56) References Cited

OTHER PUBLICATIONS

File history of U.S. Appl. No. 13/895,893, filed May 16, 2013, entitled Systems and Methods for Estimating Ischemia and Blood Flow Characteristics from Vessel Geometry and Physiology, Part 3, 50 pgs.
File history of U.S. Appl. No. 13/895,893, filed May 16, 2013, entitled Systems and Methods for Estimating Ischemia and Blood Flow Characteristics from Vessel Geometry and Physiology, Part 4, 50 pgs.
File history of U.S. Appl. No. 13/895,893, filed May 16, 2013, entitled Systems and Methods for Estimating Ischemia and Blood Flow Characteristics from Vessel Geometry and Physiology, Part 5, 50 pgs.
File history of U.S. Appl. No. 13/895,893, filed May 16, 2013, entitled Systems and Methods for Estimating Ischemia and Blood Flow Characteristics from Vessel Geometry and Physiology, Part 6, 50 pgs.
File history of U.S. Appl. No. 13/895,893, filed May 16, 2013, entitled Systems and Methods for Estimating Ischemia and Blood Flow Characteristics from Vessel Geometry and Physiology, Part 7, 50 pgs.
File history of U.S. Appl. No. 13/895,893, filed May 16, 2013, entitled Systems and Methods for Estimating Ischemia and Blood Flow Characteristics from Vessel Geometry and Physiology, Part 8, 50 pgs.
File history of U.S. Appl. No. 13/895,893, filed May 16, 2013, entitled Systems and Methods for Estimating Ischemia and Blood Flow Characteristics from Vessel Geometry and Physiology, Part 9, 50 pgs.
File history of U.S. Appl. No. 13/895,893, filed May 16, 2013, entitled Systems and Methods for Estimating Ischemia and Blood Flow Characteristics from Vessel Geometry and Physiology, Part 10, 50 pgs.
File history of U.S. Appl. No. 13/895,893, filed May 16, 2013, entitled Systems and Methods for Estimating Ischemia and Blood Flow Characteristics from Vessel Geometry and Physiology, Part 11, 11 pgs.
Khandoker et al., Investigating fetal myocardial function in heart anomalies by Doppler myocardial performance Indices, 2017 39th Annual International Conference of the IEEE Engineering in Medicine and Biology Society (EMBC), IEEE Conference Publication, 2017, pp. 2197-2200.
Feng et al., An in vitro study of the influence of monocusp patch size on the hemodynamics for reconstructing right venticular outflow tract in tetralogy, 2017 39th Annual International Conference of the IEEE Engineering Medicine & Biology Society (EMBC), pp. 1299-1302.
Khandoker et al., Assessing the development of fetal myocardial function by a novel Doppler myocardial performance index, 2016 38th Annual International Conference of the IEEE Engineering in Medicine and Biology Society (EMBC), IEEE Conference Publications, 2016, pp. 3753-3756.
Mihalef et al., Patient-specific modeling of left heart anatomy, dynamics and hemodynamics from high resolution 4D CT, 2010 IEEE International Symposium on Biomedical Imaging: From Nano to Macro Year; IEEE Conference Publications, 2010, pp. 504-507.

\* cited by examiner

MACHINE LEARNING SYSTEM FOR ASSESSING HEART VALVES AND SURROUNDING CARDIOVASCULAR TRACTS

CROSS-REFERENCE TO RELATED APPLICATION

This application is a continuation application of Ser. No. 15/138,922, filed Apr. 26, 2016 entitled "MACHINE LEARNING SYSTEM FOR ASSESSING HEART VALVES AND SURROUNDING CARIOVASCULAR TRACTS," which is a continuation application of Ser. No. 14/680,892, filed Apr. 7, 2015, now U.S. Pat. No. 9,424,531, entitled "MACHINE LEARNING SYSTEM FOR ASSESSING HEART VALVES AND SURROUNDING CARDIOVASCULAR TRACTS," which is a continuation of Ser. No. 14/511,018, filed Oct. 9, 2014, now U.S. Pat. No. 9,092,743, entitled "MACHINE LEARNING SYSTEM FOR ASSESSING HEART VALVES AND SURROUNDING CARDIOVASCULAR TRACTS," which claims priority to U.S. Provisional Patent Application No. 61/894,814, entitled "MACHINE LEARNING SYSTEM FOR ASSESSING HEART VALVES AND SURROUNDING CARDIOVASCULAR TRACTS," filed on Oct. 23, 2013. The full disclosures of the above-listed patent applications are hereby incorporated by reference herein.

FIELD

The present disclosure relates generally to the fields of machine learning, computer modeling and simulation, and computer aided design. More specifically, the disclosure relates to computer-based machine learning systems and methods for constructing and executing models of cardiac anatomy and physiology. These models may be used for therapeutic, treatment, and/or diagnostic purposes.

BACKGROUND

Cardiovascular disease is the leading cause of death in the United States and claims the lives of more than 600,000 Americans each year. According to the American Heart Association (AHA), more than five million Americans are diagnosed with heart valve disease each year, and diseases of the aortic and mitral valves are the most prevalent. Combined, aortic and mitral valve diseases affect more than five percent of the U.S. population.

The proper assessment and diagnosis of heart valve operation and the condition of surrounding cardiovascular tracts are essential for ensuring high quality patient care. To this end, several imaging modalities may be used to inspect the condition and function of heart valves and the surrounding vasculature. Transthoracic and transesogophogeal echocardiography, for example, use ultrasound technology to create two- and/or three-dimensional images of heart valves and the surrounding inflow/outflow tracts (e.g., left ventricular outflow tract, ascending aorta). Further, computed tomography (CT) and magnetic resonance imaging (MRI) may also be used.

All imaging modalities have strengths and weaknesses that may limit their ability to provide a complete and comprehensive assessment of anatomic and/or physiologic condition. The spatial resolution of echocardiographic images, for example, may inhibit a detailed analysis of functional operation, especially for highly calcified heart valves. Computed tomography may provide higher resolution images than echocardiography, but CT imaging studies are more costly and expose patients to radiation that is potentially harmful. In addition, contrast agents, which may be highly nephrotoxic and may be associated with alterations in renal function, are often used during CT examinations. Hence, new and novel methods that enable an accurate anatomic and physiological assessment of heart valves and the surrounding vasculature, while not exposing patients to excessive risks or prohibitive costs, are desirable.

Patients diagnosed with symptomatic and clinically significant heart valve abnormalities may be candidates for valvular repair or replacement. When repair or replacement is indicated, an accurate and complete understanding of valvular anatomy is essential to ensure a favorable outcome. In addition, the anatomic and physiologic characteristics of the inflow and outflow tracts that surround the heart valve(s) must also be understood.

New methods for assessing the anatomic and/or physiologic condition of native and prosthetic heart valves and the surrounding inflow/outflow tracts should enable more accurate and precise treatment planning. These new methods may complement and/or work in conjunction with existing methods, or they may stand alone. Regardless, such technologies must provide clear and demonstrable benefits to the physician(s) who treat patients with heart valve disease and/or diseases of the surrounding cardiac tracts. Further, new technologies must not expose patients to excessive medical risks and should be cost effective.

Therefore, to improve diagnostic and treatment capabilities, it is desirable to have a system for quickly and accurately assessing the physiological function, condition, and morphology of heart valves and the surrounding inflow/outflow tracts, which thereby enables the proper diagnosis of heart valve disease and, if warranted, facilitates treatment planning.

DESCRIPTION OF RELATED ART

There are many academic and industrial research groups that use computer modeling and simulation to analyze flow through heart valves. Historically, valvular hemodynamic analyses have focused on the aortic heart valve and have employed methods of computational fluid dynamics (CFD) to provide detailed insight into the blood flow surrounding the aortic valve. These insights have then been used to facilitate the design and construction of heart valves with desirable hemodynamic properties that maximize functionality and durability while minimizing the potentially fatal risks of valvular malfunction and adverse physiological response.

In recent years, hemodynamic modeling of heart valves has included both surgically implanted and transcatheter prostheses, but the focus of most studies remains the aortic valve. With the rapidly expanding clinical deployment of transcatheter aortic heart valves, modeling and simulation results have helped understand and characterize the unique hemodynamic challenges of transcatheter designs compared to traditional surgical implantation of aortic valves. In particular, computer modeling may be used to quantify downstream flow effects in the aortic arch and leaflet stresses, which impact device efficacy, robustness, durability, and longevity.

To date, all computer modeling and simulation studies of heart valves have been focused on evaluating and improving prosthetic valve design and function.

BRIEF SUMMARY OF THE PRESENT INVENTION

The machine learning system and method described in this disclosure facilitates the diagnosis and treatment of heart valve disease and diseases of the surrounding inflow/outflow tracts. Further, the system and method facilitate the evaluation and assessment of valvular repair and/or prosthetic performance in patients who have undergone heart valve treatment. In addition to using routine physiological and geometric data gathered through two- and/or three-dimensional imaging studies, the machine learning system may also incorporate hemodynamic data into the construction and utilization of an accurate geometric and functional understanding from which to assess valvular condition and function.

In one aspect, a machine learning system for evaluating at least one characteristic of a heart valve, an inflow tract and/or an outflow tract may include a training mode and a production mode. The training mode may be configured to train a computer and construct a transformation function to predict an unknown anatomical characteristic and/or an unknown physiological characteristic of a heart valve, an inflow tract and/or an outflow tract, using a known anatomical characteristic and/or a known physiological characteristic of the heart valve, inflow tract and/or outflow tract. The production mode may be configured to use the transformation function to predict the unknown anatomical characteristic and/or the unknown physiological characteristic of the heart valve, inflow tract and/or outflow tract, based on the known anatomical characteristic and/or the known physiological characteristic of the heart valve, inflow tract and/or outflow tract.

In some embodiments, the training mode is configured to compute and store in a feature vector the known anatomical characteristic and/or known physiological characteristic of the heart valve, inflow tract and/or outflow tract. In some embodiments, the training mode is configured to calculate an approximate blood flow through the heart valve, inflow tract and/or outflow tract. In some embodiments, the training mode is further configured to store quantities associated with the approximate blood flow through the heart valve, inflow tract and/or outflow tract. Optionally, the training mode may be further configured to perturb the at least one known anatomical characteristic or known physiological characteristic of the heart valve, inflow tract and/or outflow tract stored in the feature vector. In some embodiments, the training mode may be further configured to calculate a new approximate blood flow through the heart valve, inflow tract and/or outflow tract with the perturbed known anatomical characteristic and/or known physiological characteristic. In some embodiments, the training mode may be further configured to store quantities associated with the new approximate blood flow through the perturbed heart valve, inflow tract and/or outflow tract. In some embodiments, the training mode may be further configured to repeat the perturbing, calculating and storing steps to create a set of feature vectors and quantity vectors and to generate the transformation function.

In one embodiment, the training mode may be further configured to perform a method, involving: receiving patient-specific data including anatomic data, physiologic data and/or hemodynamic data; generating a digital model of the at least one heart valve, inflow tract or outflow tract, based on the received data; discretizing the digital model; applying boundary conditions to at least one inflow portion and at least one outflow portion of the digital model; and initializing and solving mathematical equations of blood flow through the digital model. In some embodiments, the method may further involve storing quantities and parameters that characterize an anatomic state and/or a physiologic state of the digital model and the blood flow. In some embodiments, the method may further involve perturbing an anatomic parameter and/or a physiologic parameter that characterizes the digital model. In another embodiment, the method may further involve re-discretizing and/or re-solving the mathematical equations with the anatomic parameter and/or physiologic parameter. In another embodiment, the method may further involve storing quantities and parameters that characterize the anatomic state and/or the physiologic state of the perturbed model and blood flow.

In some embodiments, the production mode may be configured to receive one or more feature vectors. In some embodiments, the production mode may be configured to apply the transformation function to the feature vectors. In some embodiments, the production mode may be configured to generate one or more quantities of interest. In some embodiment, the production mode may be configured to store the quantities of interest. In some embodiments, the production mode may be configured to process the quantities of interest to provide data for use in at least one of evaluation, diagnosis, prognosis, treatment or treatment planning related to a heart in which the heart valve resides.

In another aspect, a computer-implemented machine learning method for evaluating at least one characteristic of a heart valve, an inflow tract, and/or an outflow tract may involve training a computer by using a training mode of a machine learning system to construct a transformation function to predict an unknown anatomical characteristic and/or an unknown physiological characteristic a heart valve, an inflow tract and/or an outflow tract, using a known anatomical characteristic and/or a known physiological characteristic of the heart valve, inflow tract and/or outflow tract. The method may also involve using a production mode of the machine learning system to direct the transformation function to predict the unknown anatomical characteristic and/or the unknown physiological characteristic of the heart valve, inflow tract and/or outflow tract, based on the known anatomical characteristic and/or the known physiological characteristic of the heart valve, inflow tract and/or outflow tract.

In some embodiments, the method may further involve using the training mode to compute and store in a feature vector the known anatomical characteristic and/or known physiological characteristic of the heart valve, inflow tract and/or outflow tract. In some embodiments, the method may further involve using the training mode to calculate an approximate blood flow through the heart valve, inflow tract and/or outflow tract. In some embodiments, the method may further involve using the training mode to store quantities associated with the approximate blood flow through the heart valve, inflow tract and/or outflow tract. In some embodiments, the method may further involve using the training mode to perturb the known anatomical characteristic and/or known physiological characteristic of the heart valve, inflow tract and/or outflow tract stored in the feature vector. In some embodiments, the method may further involve using the training mode to calculate a new approximate blood flow through the heart valve, inflow tract and/or outflow tract with the perturbed known anatomical characteristic and/or known physiological characteristic. In some embodiments, the method may further involve using the training mode to store quantities associated with the new approximate blood flow through the perturbed heart valve, inflow tract and/or outflow tract. In some embodiments, the method may further involve using the training mode to repeat the perturbing, calculating and storing steps to create a set of feature vectors and quantity vectors and to generate the transformation function.

In some embodiments, the method may further involve using the training mode to perform the following steps: receiving patient-specific data selected from the group consisting of anatomic data, physiologic data, and hemodynamic data; generating a digital model of the at least one heart valve, inflow tract or outflow tract, based on the received data; discretizing the digital model; applying boundary conditions to at least one inflow portion and at least one outflow portion of the digital model; and initializing and solving mathematical equations of blood flow through the digital model. In some embodiments, the method may further involve storing quantities and parameters that characterize an anatomic state and/or a physiologic state of the digital model and the blood flow. In some embodiments, the method may further involve perturbing an anatomic parameter and/or a physiologic parameter that characterizes the digital model. In some embodiments, the method may further involve re-discretizing or re-solving the mathematical equations with the at least one anatomic parameter or physiologic parameter. In some embodiments, the method may further involve storing quantities and parameters that characterize the anatomic state and/or the physiologic state of the perturbed model and blood flow.

In some embodiments, the method may further involve receiving one or more feature vectors with the production mode. In some embodiments, the method may further involve using the production mode to apply the transformation function to the feature vectors. In some embodiments, the method may further involve using the production mode to generate one or more quantities of interest. In some embodiments, the method may further involve using the production mode to store the quantities of interest. In some embodiments, the method may further involve using the production mode to process the quantities of interest to provide data for use in evaluation, diagnosis, prognosis, treatment and/or treatment planning related to a heart in which the heart valve, inflow tract and/or outflow tract resides.

In another aspect, a non-transitory computer readable medium for use on a computer system may contain computer-executable programming instructions for performing a method for evaluating at least one characteristic of a heart valve, an inflow tract, an outflow tract or a combination thereof. The method may include any of the features and/or aspects described above.

In various other aspects, this disclosure describes various method embodiments. Examples of such method embodiments include: A method of using data analysis and/or machine learning to construct a transformation function to compute the anatomic and/or physiologic state of at least one heart valve and/or the corresponding inflow/outflow tracts; A method of using computer modeling and simulation and/or clinical data to generate a set of feature vectors that are used as input into a machine learning algorithm; A method of using machine learning to assess anatomy and/or physiology of at least one heart valve and/or the corresponding inflow/outflow tracts, comprising using patient-specific data derived from one or more interventional or non-interventional methods and/or results generated by computer modeling and simulation; A method of using machine learning to assess the anatomy and/or physiology of at least one heart valve and/or the corresponding inflow/outflow tracts, comprising using patient-specific data derived from one or more interventional or non-interventional methods to perform sensitivity and uncertainly analyses; A method of using machine learning to assess the anatomy and/or physiology of at least one heart valve and/or the corresponding inflow/outflow tracts, comprising using patient-specific data derived from one or more interventional or non-interventional methods to aid in the diagnosis, assessment and/or prognosis of a diseased state; and A method of using machine learning to assess the anatomy and/or physiology of at least one heart valve and/or the corresponding inflow/outflow tracts, comprising using patient-specific data derived from one or more interventional or non-interventional methods to aid in the planning of prosthetic heart valve implantation.

These and other aspects and embodiments will be described in further detail below, in reference to the attached drawing figures.

DETAILED DESCRIPTION

This disclosure describes machine learning systems and methods that qualitatively and quantitatively characterize anatomic geometry and/or physiology of a heart valve, one or more inflow tracts of a heart valve, and/or one or more outflow tracts of a heart valve. Throughout this disclosure, reference may be made to characterizing or evaluating a heart valve. In all embodiments, such characterization, evaluation, etc. may be performed on a heart valve, one or more inflow tracts of a heart valve, and/or one or more outflow tracts of a heart valve. For enhanced readability of the description, however, the phrase "heart valve" may simply be used, rather than repeating "a heart valve, one or more inflow tracts of a heart valve, and/or one or more outflow tracts of a heart valve" in each instance. Any embodiment described for use in evaluating a heart valve may additionally or alternatively be used to evaluate one or more inflow tracts of a heart valve and/or one or more outflow tracts of a heart valve. The various embodiments described herein may be applied to any single heart valve, a combination of multiple heart valves, and/or combinations of one or more heart valves and one or more coronary blood vessels. Although occasional references may be made to one specific heart valve, inflow tract, or outflow tract, these specific references should not be interpreted as limiting the scope of this disclosure. For example, the aortic heart valve is used throughout this disclosure as a specific example of a prototypical heart valve. Illustration of the systems and methods via the example of the aortic heart valve, however, is not intended to limit the scope of the computer modeling and simulation systems and methods disclosed herein.

Figure 1:
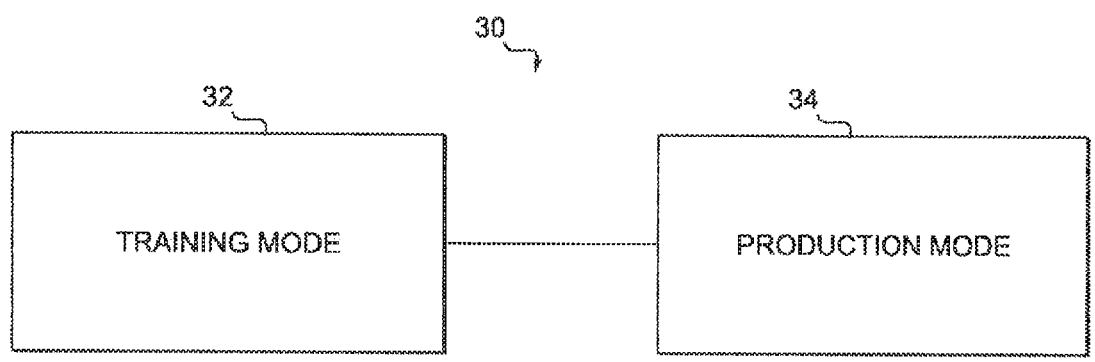
FIG. 1 is a block diagram of a machine learning system, according to one embodiment.

Referring to FIG. 1 and according to one embodiment, a machine learning system 30 may include two modes: a training mode 32 and a production mode 34. The two modes 32, 34 may be embodied in a computer system and/or a computer readable medium. The system 30 may execute the two modes in series, where the training mode 32 is executed first, and the production mode 34 is executed second. The training mode 32 may be configured to develop analytical capabilities in a computer system that enable the computer system to predict unknown anatomic and/or physiologic characteristics of one or more heart valves and/or the surrounding inflow/outflow tracts. These predictive capabilities may be developed by the analysis and/or evaluation of known anatomic and/or physiologic characteristics of one or more heart valves and/or the surrounding inflow/outflow tracts. Using a collection of known anatomic and/or physiologic characteristics, a computer may be "trained" to predict various unknown anatomic and/or physiologic characteristics. The abstract mapping that transforms a set of known characteristics into one or more predictions of unknown characteristics may be referred to as the "transformation function." In some embodiments, the training mode 32 may be configured to construct the transformation function.

The production mode 34 of the machine learning system 30 may use the transformation function to predict anatomic and/or physiologic characteristics that are unknown from a collection of anatomic and/or physiologic characteristics that are known. Hence, during execution of the production mode 34, input into the transformation function may be a set of known anatomic and/or physiologic characteristics (e.g., the same anatomic and/or physiologic characteristics used during the training mode 32). The output of the transformation function may be one or more anatomic and/or physiologic characteristics that were previously unknown.

The training mode 32 and production mode 34 may be implemented in a number of different ways in various alternative embodiments. One embodiment of a method for implementing the training mode 32 and production mode 34 of a machine learning system is described in more detail immediately below. This is only one exemplary embodiment, however, and should not be interpreted as limiting the scope of the machine learning system 30 as described above.

Training Mode:

During the training mode 32 of the machine learning system 30, anatomic and/or physiologic data may be acquired that characterize the state and operation of a heart valve and its corresponding inflow/outflow tracts. These data may be collected through one or more acquisition methods, including, for example, analysis of radiological images, analysis of echocardiographic images, Doppler and/or electrophysiologic signals, clinical instruments (e.g., blood pressure gauge, stethoscope), and computer modeling/simulation. Referring to the aortic valve as an example, anatomic and/or physiologic characterization parameters may include, for example:

flow characteristics (e.g., velocities, velocity gradients, pressures, pressure gradients, turbulence intensity, shear stress) at single or multiple location(s) within the left ventricular outflow tract (LVOT), valsalva sinuses (VS), sinotubular junction (SJ), ascending aorta (AA) or vasculature surrounding one or more heart valve(s);

approximations to flow, flow properties or flow characteristics via simplified and/or analytical models (e.g., pipe flow, orifice flow);

size and/or shape characteristics at single or multiple location(s) within the LVOT, VS, SJ, AA, or surrounding vasculature, e.g., diameter, eccentricity, cross-sectional area, axial length, length of major axis, length of minor axis, geometric gradient(s);

height, shape, lateral profile, thickness, degree of calcification, location of calcification, angular size, angular separation, radial length, tip sharpness, rigidity, flexibility, movement, tissue properties, overlap, and/or attachment angle(s) of one or more valve leaflets;

location, attachment angles, and/or sizes of one or more coronary arteries;

geometric orifice area and/or estimated orifice area of the valve;

size, shape, location, density, composition, and/or extent of vascular calcification;

stroke volume and/or cardiac output;

blood pressure, heart rate, and/or hematocrit of the patient; and age, height, weight, body mass index, race, and/or gender of the patient.

Figure 2:
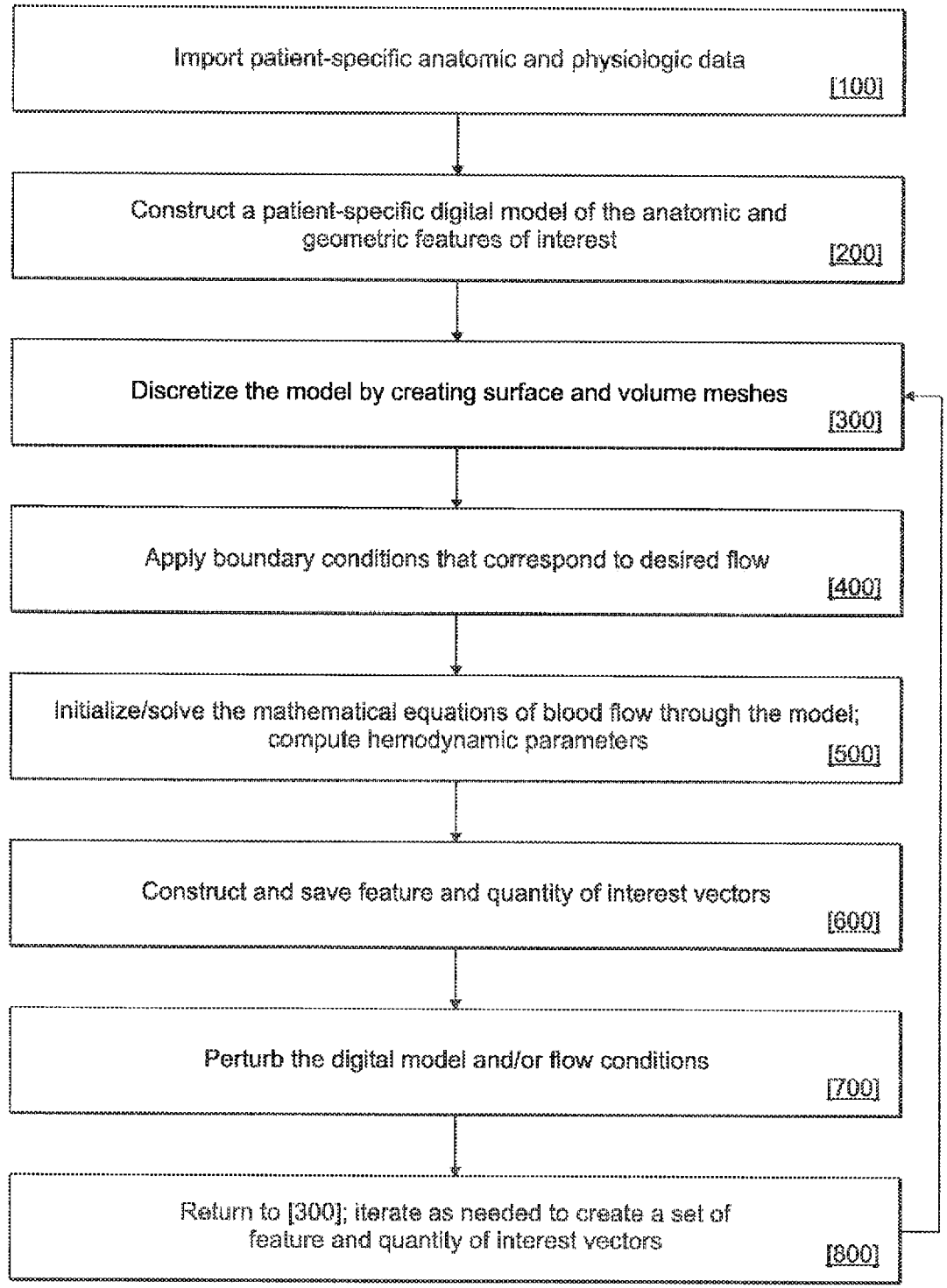
FIG. 2 is a flow diagram outlining a modeling and simulation method for a training portion of a machine learning system, according to one embodiment.

Referring to FIG. 2, one embodiment of a method for implementing the training mode 32 of the machine learning system 30 is illustrated. In this embodiment, the training mode 32 of the machine learning system 30 is coupled with a modeling and simulation system (not shown), which may provide input data for the machine learning system 30. Hence, the modeling and simulation system may operate in conjunction with the machine learning system 30, in that it may provide anatomic and/or physiologic data to the machine learning system 30. These data may serve as the foundation from which the machine learning system 30 learns to perform the desired task(s).

A first step of the embodiment described in FIG. 2 may involve importing patient-specific geometric, anatomic, physiologic, and/or hemodynamic data into the computer system 100. A second step may involve constructing a (possibly parameterized) geometric model using the imported data 200. One embodiment of a geometric model 10 is illustrated in FIG. 5.

Figure 5:
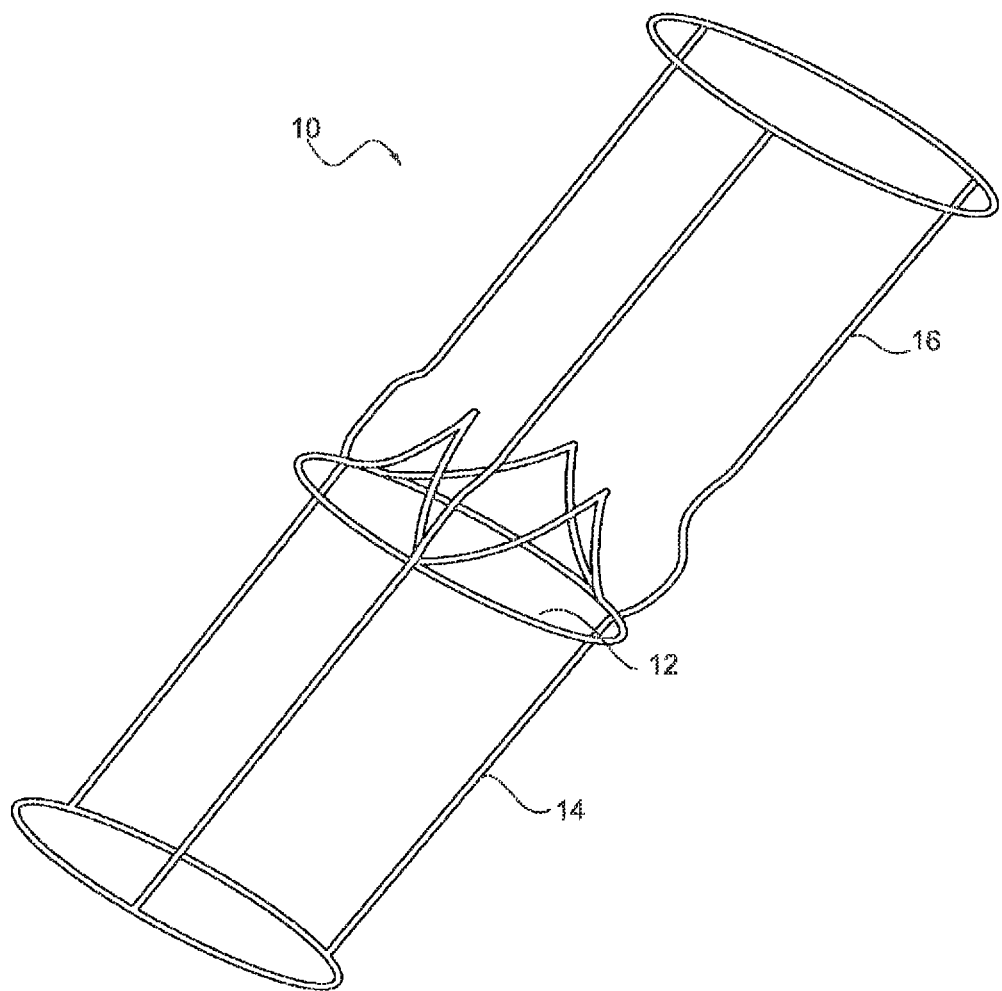
FIG. 5 is a perspective view of a simplified geometric model, based on patient-specific anatomic parameters, of an aortic valve and surrounding cardiac inflow and outflow vessels, according to one embodiment.

As illustrated in FIG. 5, in one embodiment, the geometric model 10 may be a multi-dimensional digital representation of the relevant patient anatomy, which may include at least one heart valve 12 (the aortic valve in one embodiment), at least a portion of an inflow vessel 14 (or "inflow tract"), and at least a portion of an outflow vessel 16 (or "outflow tract") of the valve 12. The model may also include one or more ventricles and/or atria of the heart or a portion thereof and/or one or more coronary vessels or a portion thereof. The geometric model is created from patient-specific anatomical, geometric, physiologic, and/or hemodynamic data. In some embodiments, the model may be created using exclusively imaging data. Alternatively, the model may be created using imaging data and at least one clinically measured flow parameter. Imaging data may be obtained from any suitable diagnostic imaging exam(s), such as those listed above. Clinically measured flow parameters may be obtained from any suitable test(s), such as those listed above.

The model 10 may also contain at least one inflow boundary and at least one outflow boundary, through which blood flows in and out of the multi-dimensional model 10, respectively. These inflow and outflow boundaries denote finite truncations of the digital model 10 and are not physically present in a patient. The digital geometric model 10 may be created using methods of applied mathematics and image analysis, such as but not limited to image segmentation, machine learning, computer aided design, parametric curve fitting, and polynomial approximation. In some embodiments, a hybrid approach, which combines a collection of geometric modeling techniques, may also be utilized. The final, multi-dimensional model 10 provides a digital surrogate that captures the relevant physical features of the anatomic topology under consideration and may contain one or more morphological simplifications (e.g., symmetry, smoothing) that exploit the underlying geometric features of the patient-specific valvular and vascular system being considered.

Referring again to FIG. 1, following the construction of the digital model 200, the modeling and simulation portion of the machine learning system may discretize the surface and volume of the model into a finite number of partitions 300. These individual and non-overlapping partitions, called "elements," may facilitate the application and solution of the physical laws of motion that govern blood flow through the geometric model. The set of surface and volume elements used to discretize the model, collectively referred to as the "mesh," transform the continuous geometric model into a set of mesh points and edges, where each element point in the mesh has discrete x, y, and z spatial coordinates, and each element edge is bounded by two mesh points and has a finite length.

Figure 6:
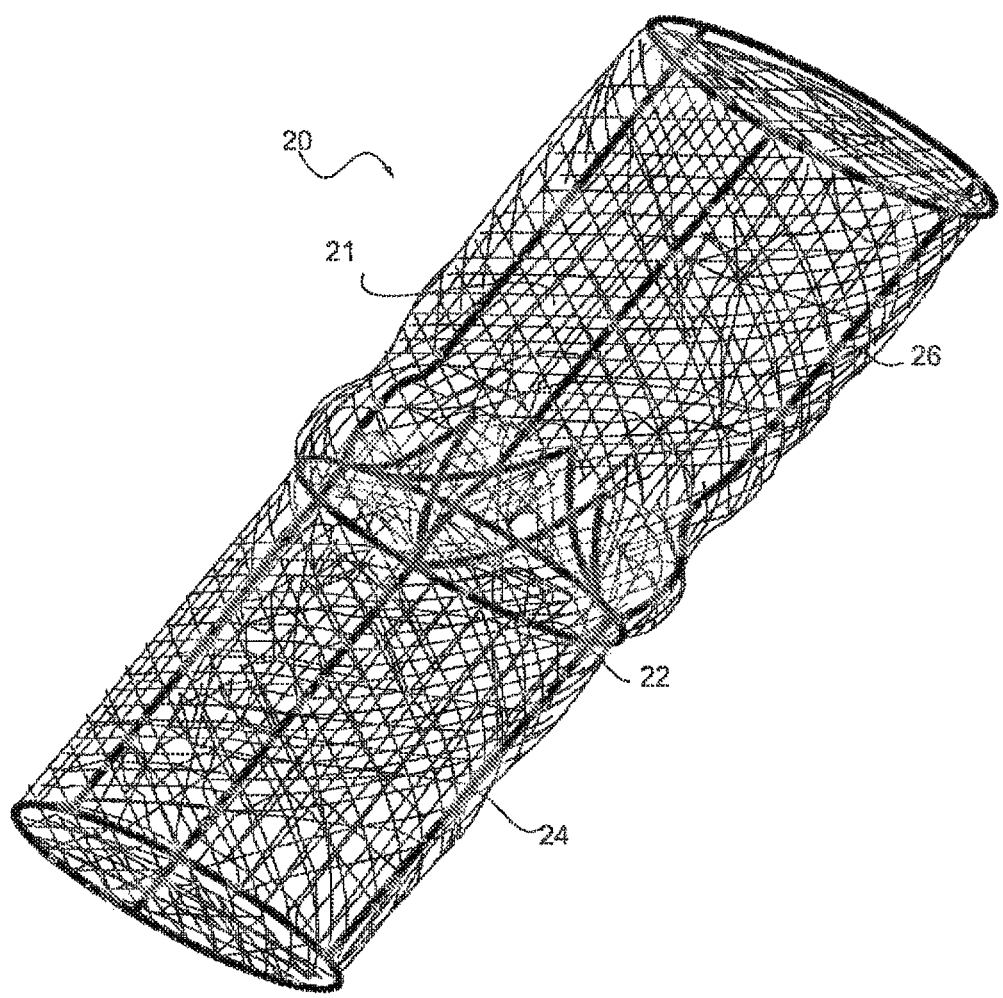
FIG. 6 is a perspective view of a simplified geometric model with the computational surface mesh, based on patient-specific anatomic parameters, of the aortic valve and the surrounding cardiac inflow and outflow vessels, according to one embodiment.
Figure 7A:
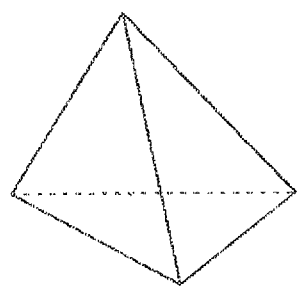
FIGS. 7A-7D are perspective views of various representative polyhedra used to discretize the interior volume of the geometric model, according to various embodiments.
Figure 7B:
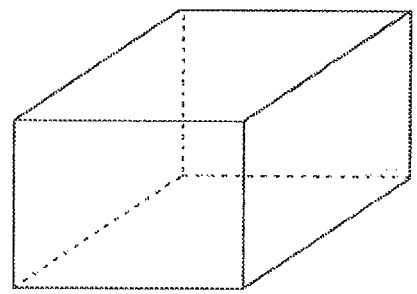
Figure 7C:
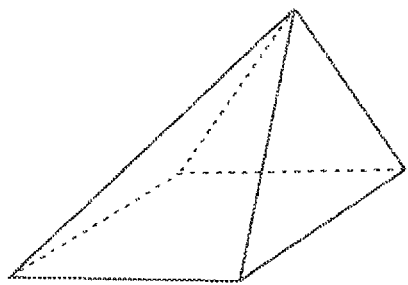
Figure 7D:
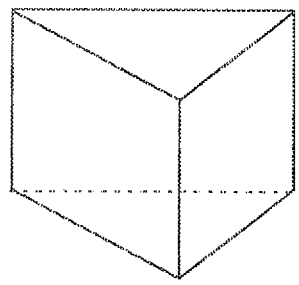

An illustration of a representative mesh 21 that discretizes the surface of a geometric model 20 is shown in FIG. 6. The geometric model 20, in this embodiment, includes an aortic valve 22, inflow tract 24 and outflow tract 26. This illustration of the model 20 is used to show the mesh 21 and is intended for exemplary purposes only.

The shape of the surface elements created by the modeling and simulation portion of the machine learning system may take the form of any closed polygon, but the surface mesh typically contains a collection of triangles, convex quadrilaterals or a combination thereof. Referring to FIGS. 7A-7D, volume elements may be created by the modeling and simulation system and are used to fill the interior of the model completely. Each volume element may take the form of any closed polyhedron, but the volume mesh (i.e., the set of volume elements) typically contains a collection of tetrahedra (FIG. 7A), hexahedra (FIG. 7B), pyramids (FIG. 7C), wedges (FIG. 7D), or a combination thereof. The surface and volume mesh densities, which determine the spatial resolution of the discrete model, may vary in space and time. The local densities of the surface and volume meshes may depend on the complexity of the local topology of the underlying geometric model: more complex local topology may require higher spatial resolution, and therefore a higher mesh density, to resolve than local regions of less complex topology.

The modeling and simulation portion of the machine learning method may use CFD to simulate blood flow through the discretized geometric model. Blood may be represented as a Newtonian or non-Newtonian fluid, and blood flow may be represented physically by the conservation of mass, momentum, and energy (or a combination thereof) and mathematically by the fluid flow equations (e.g., continuity, Navier-Stokes equations) with appropriate initial and boundary conditions. The boundary conditions may be a function of time and/or space. Initial and boundary conditions may be determined from empirical or heuristic relationships, clinical data, mathematical formulas or a combination thereof, and the model boundaries may be rigid or compliant or a combination thereof. The mathematical equations and corresponding initial and boundary conditions may be solved using conventional mathematical techniques, which include analytical or special functions, numerical methods (e.g., finite differences, finite volumes, finite elements, spectral methods), methods of machine learning or a hybrid approach that combines various aspects of the methods listed.

As a next step in the modeling and simulation portion of the machine learning method, and referring again to FIG. 2, boundary conditions may be applied to a discrete patient model 400. The boundary flow conditions may be obtained from patient-specific clinical measurements (e.g., pulse wave Doppler echocardiography, continuous wave Doppler echocardiography, MRI), in which case they may be prescribed to the model in a manner that is consistent with clinical observations and measurements. In addition, inflow and outflow boundary conditions may be prescribed to compensate for underlying psychological or medical conditions such as pain, anxiety, fear, anemia, hyperthyroidism, left ventricular systolic dysfunction, left ventricular hypertrophy, hypertension or arterial-venous fistula, which may produce clinically misleading results upon which medical evaluations, diagnostics, treatment planning or treatment(s) may be based.

With continued reference to FIG. 2, following the initialization of the blood flow equations, the equations are solved, and hemodynamic quantities of interest are computed 500 by the modeling and simulation system, which may be a component of the training mode 32 of the machine learning system 30. The hemodynamic quantities of interest computed by the modeling and simulation system may include, for example, the flow velocity at one or more points in the computational domain, velocity gradients, pressure, pressure gradients, shear stress, the wall shear stress at location (s) on the heart valve, etc.

Following the solution of the mathematical equations and computation of the quantities of interest, the anatomic and physiologic parameters that are inputs into the modeling and simulation system, collectively referred to as "features," may be assembled into a vector 600. This vector of anatomic and physiologic features is referred to as a "feature vector." As an illustrative example, numerical quantities contained in a feature vector may include some or all of the parameters (or features) outlined above, e.g., LVOT diameter, LVOT velocity, LVOT cross sectional area, height of each valvular leaflet, thickness of each valvular leaflet, diameter of the ascending aorta, etc. The corresponding hemodynamic quantities of interest, which may be computed from the CFD simulation from an anatomic model that may be characterized by features in the feature vector, may also assembled into a vector, which may be referred to as the "quantity of interest vector." The quantity of interest vector may include, for example, wall shear stress, pressure, pressure gradients, velocity, velocity gradients, and/or shear at various locations throughout the model, etc. Both the feature and quantity of interest vectors may then be saved for use during other steps of the machine learning process. Note that a feature vector and the corresponding quantity of interest vector may have different lengths. In addition, entries within the feature and quantity of interest vector may be obtained from different mechanisms (e.g., clinical data, numerical simulations, estimated approximation). Nonetheless, each feature vector is associated with a quantity of interest vector and vice versa.

Referring to FIG. 2, a next step in the method may involve modifying (or "perturbing") the digital model and/or flow condition to represent perturbed anatomic and/or physiologic conditions 700. As an example of an anatomic perturbation, one valve leaflet may be retracted to increase the geometric orifice area of the valve. As an example of a physiologic perturbation, the inflow velocity through the LVOT may be increased or decreased.

As illustrated in FIG. 2, following modification(s) to the anatomic and/or physiologic conditions 700, steps 300-700 of the modeling and simulation portion of the machine learning system may be repeated 800, until a desired number of feature vectors and the corresponding quantities of interest vectors are obtained. Note that each iteration of steps 300-700 produces a new feature vector and a new quantity of interest vector. Though one or more entries within the feature and/or quantity of interest vector may change with each iteration of steps 300-700, the representation and length of each vector remains the same. That is, each digital model is represented by the same characteristics and the same number of characteristics, and this collection of characteristics is contained within the feature vector. Further, the corresponding quantities of interest for each digital model are the same. The sets of feature and quantity of interest vectors may then be stored on digital media.

Figure 3:
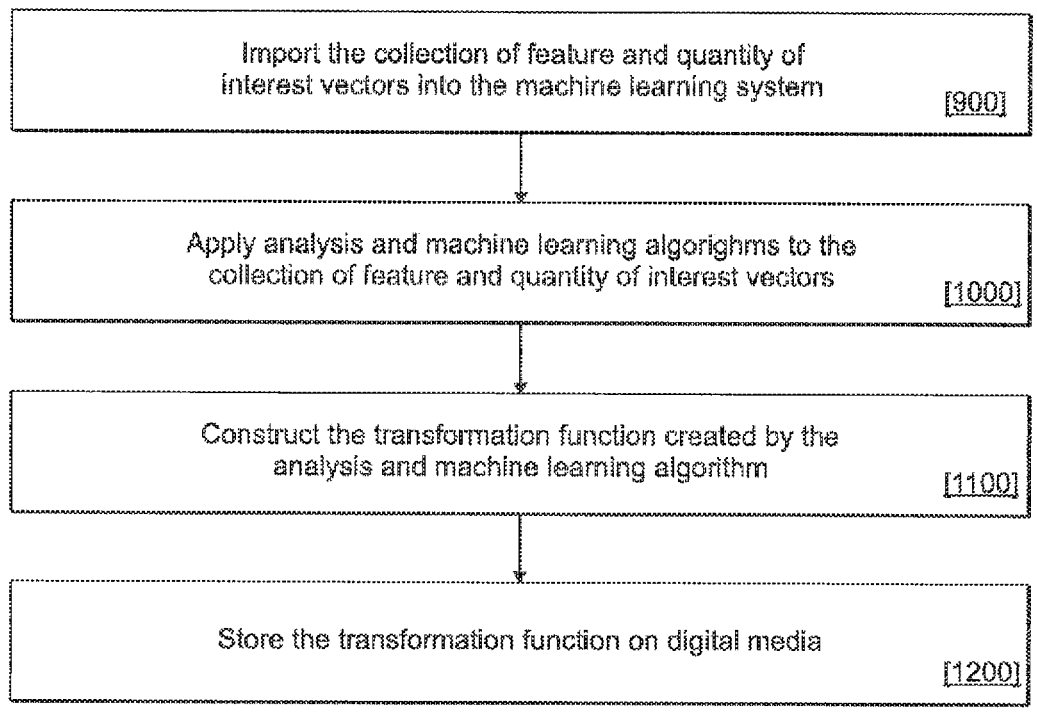
FIG. 3 is a flow diagram outlining execution of a training portion of a machine learning system, according to one embodiment.

In some embodiments, and referring now to FIG. 3, a machine learning method may involve applying machine learning algorithms to a collection of feature and quantity of interest vectors from the method described above and illustrated in FIG. 2. The collection of feature and quantity of interest vectors may first be imported into machine learning software 900. The machine learning software may then apply one or more analysis or machine learning algorithms (e.g., decision trees, support vector machines, regression, Bayesian networks, random forests) to the set of feature and quantity of interest vectors 1000. Following the application of machine learning algorithm(s), a transformation function is constructed 1100. This transformation function may serve as a mapping between the one or more features contained within a feature vector and the one or more quantities of interest computed from the modeling and simulation portion of the machine learning system. Hence, the input into the transformation function is a feature vector, and the output of the transformation function is a quantity of interest vector. To test the accuracy of the transformation function created by the machine learning algorithm, for example, one of the feature vectors used to create the transformation function may be used as input into the transformation function. The expected output from the transformation function is the corresponding quantity of interest vector, though the quantity of interest output vector may not be reproduced exactly by the transformation function. The transformation function may be stored on digital media for use, for example, during the production mode of the machine learning system 1200.

Following construction of the transformation function by the analysis and machine learning algorithm(s), functioning of the training mode 32 of the machine learning system 30, as described in the present embodiment, may be complete. Subsequently, the transformation function may be used in the production mode 34 of the machine learning system 30.

Production Mode:

The production mode 34 of the machine learning system 30 may be used after the training mode 32. The production mode 34 may be configured to compute quantity of interest vectors rapidly and accurately by applying the transformation function to a variety of feature vectors. In some but not all cases, these feature vectors might have been used to construct the transformation function.

Figure 4:
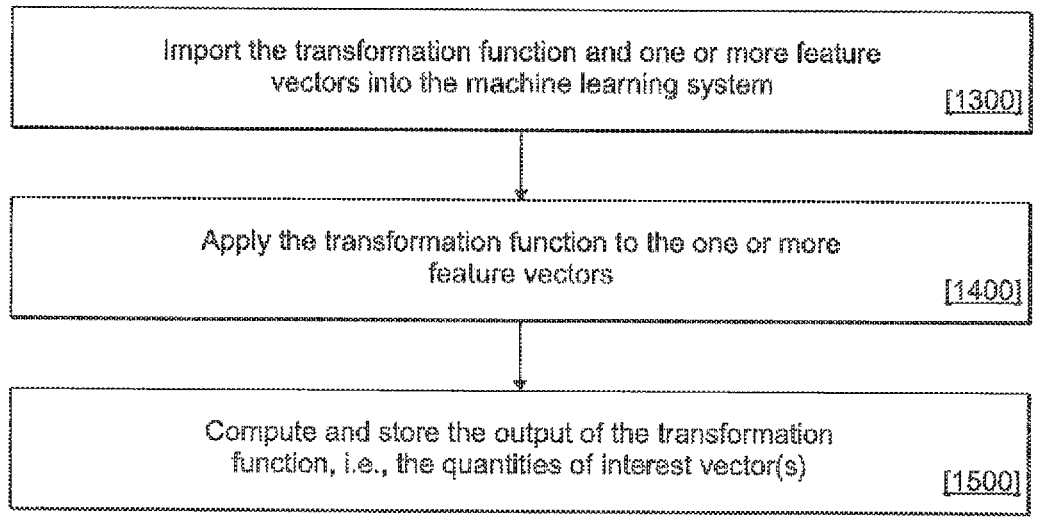
FIG. 4 is a flow diagram outlining execution of a production portion of a machine learning system, according to one embodiment.

Referring now to FIG. 4, in one embodiment, the production mode 34 of the machine learning system 30 may first be used to import the transformation function and one or more feature vectors 1300, which contain the same set of features used during the training mode 32. The feature vectors used during the production mode 34 may or may not have been used during the training mode to construct the transformation function, and therefore the transformation function may not have been constructed with data contained within these feature vectors. The number of features within each feature vector and the quantities represented by each feature within each feature vector, however, are the same as those used to construct the transformation function.

The transformation function may then be applied to the one or more feature vectors 1400. Hence, the inputs to the transformation function during the production mode 34 of the machine learning system 30 may be one or more feature vectors, and the output from the transformation function may be a vector that contains the quantities of interest. The quantity of interest vector outputted from the transformation function may then be stored 1500, e.g., on digital media.

The quantities of interest contained within the quantity of interest vector may include qualitative and/or quantitative geometric and hemodynamic information. These data may be further analyzed and assessed through various mechanisms of post-processing to reveal patient-specific anatomic and/or physiologic and/or hemodynamic information that may aid in the diagnosis, treatment, and/or treatment planning of a patient. These qualitative and quantitative data may also be used to guide clinical decision-making and/or provide predictive information about disease progression or risk stratification.

Quantities of interest and/or data derived from the machine learning system 30 may be delivered to physicians, who may use these data for clinical decision-making. Delivery of patient-specific information to physicians may occur via integrated or stand-alone software systems, numerical data, graphs, charts, plots, verbal discussions, written correspondence, electronic media, etc. or a combination thereof. These data may then be used by an individual physician or by a team of physicians to develop a complete, comprehensive, and accurate understanding of patient cardiac health and to determine whether or not medical treatment is warranted. If medical treatment is warranted, results from the machine learning system 30 may be used to guide clinical decision-making. By way of example, specific ways in which output from the machine learning system 30 may be incorporated into the clinical management of cardiac patients include:

analysis of heart valve operation, including diagnosing the severity, functional significance, and clinical response to abnormal heart valve operation;

patient-specific selection, sizing, and positioning of prosthetic heart valves, including surgical, transcatheter, and valve-in-valve treatments; and patient monitoring and/or follow-up.

The list of applications outlined above is for example purposes only, and the list is not intended to be exhaustive.

The machine learning system 30 may provide a fast and accurate virtual framework for conducting patient-specific sensitivity analyses. Such analyses may assess the relative impacts of geometric and/or hemodynamic changes to the anatomic, physiologic, and/or hemodynamic state of a patient; these state changes may then be assessed for functional and clinical significance thereby estimating patient response to therapy (or lack thereof), disease progression, and/or patient-specific risk stratification. Sensitivity analyses may be performed, for example, by applying the transformation function, which is computed during the training mode 32 of the machine learning system 30, to multiple feature vectors that describe variations of specific anatomic and/or physiologic features of the patient. Although construction of the transformation function during the training mode 32 is likely best to include feature vectors that are similar to those used during a sensitivity analysis, it is important to note that the transformation function may not require re-computation during a sensitivity analysis study. Hence, the machine learning system 30 may enable a rapid evaluation of numerous anatomic, physiologic, and/or hemodynamic scenarios that run in a virtual environment without exposing patients to any medical risks. Results from the plethora of transformation function evaluations conducted during a sensitivity analysis may be aggregated and presented to physicians for clinical decision-making. Further, results from sensitivity analyses may also be used in conjunction with uncertainty analyses to, for example, assess global and/or local uncertainties of anatomic, physiologic, and/or hemodynamic results produced by the machine learning system 30.

The machine learning system 30 enables planning of heart valve replacement therapy and the selection of optimal valve deployment. For example, executing the machine learning system 30 described herein provides an accurate assessment of anatomic, physiologic, and/or hemodynamic consideration for valvular deployment and function, e.g., size, deployment mechanism, deployment angle. Hence, the machine learning system 30 and methods for using it provide a complete framework that enables the accurate assessment of anatomic structure in relation to native and prosthetic heart valves and their corresponding inflow/outflow tracts. This information may be used by physicians to make clinical decisions regarding patient treatment of heart valve disease as to maximize the benefits to each patient.

Although the above description highlights a number of embodiments and examples, the present invention extends beyond the specifically disclosed embodiments to other alternative embodiments and/or uses of the invention and modifications and equivalents thereof. Thus, the scope of the present invention should not be limited by the particular disclosed embodiments described above, but should be determined only by a fair reading of the claims that follow.

I claim:

1. A computer-implemented machine learning method for evaluating at least one characteristic of a heart valve, an inflow tract, an outflow tract or a combination thereof the method comprising:
   (a) predicting, with a transformation function on a computer, at least one of an unknown anatomical characteristic or an unknown physiological characteristic of at least one of a heart valve, an inflow tract or an outflow tract, using at least one of a known anatomical characteristic or a known physiological characteristic of the at least one heart valve, inflow tract or outflow tract, wherein said at least one of said heart valve, said inflow tract, and said outflow tract includes at least one of said heart valve, a heart ventricle, and a heart atrium; and
   (b) using a production mode of a machine learning system on the computer to direct the transformation function and one or more feature vectors, to predict at least one of unknown anatomical characteristic or unknown physiological characteristic of at least one production heart valve, production inflow tract or production outflow tract, based on at least one of patient specific patient known anatomical characteristic or patient known physiological characteristic of the at least one production heart valve, production inflow tract or production outflow tract, wherein said at least one of said production heart valve, said production inflow tract, said production outflow tract includes at least one of said production heart valve, a production heart ventricle, and a production heart atrium, to generate at least one or more quantities of interest.

2. A method as in claim 1 further maintaining, in said at least one or more feature vectors on the computer, the at least one patient known anatomical characteristic or patient known physiological characteristic of the at least one production heart valve, production inflow tract or production outflow tract.

3. A method as in claim 2 further comprising using the computer to calculate an approximate blood flow through the at least one production heart valve, production inflow tract or production outflow tract.

4. A method as in claim 2, further comprising using the computer to store in at least one of said one or more feature vectors quantities associated with an approximate blood flow through the at least one production heart valve, production inflow tract or production outflow tract.

5. A method as in claim 2, further comprising using the computer to perturb the at least one patient known anatomical characteristic or patient known physiological characteristic of the at least one production heart valve, production inflow tract or production outflow tract stored in the at least one of said one or more feature vectors.

6. A method as in claim 5, further comprising using the computer to calculate a new approximate blood flow through the at least one production heart valve, production inflow tract or production outflow tract with the perturbed at least one known patient anatomical characteristic or patient known physiological characteristic.

7. A method as in claim 5, further comprising using the computer to store quantities associated with a new approximate blood flow through the perturbed at least one production heart valve, production inflow tract or production outflow tract in said one or more feature vectors.

8. A method as in claim 7, further comprising using the computer to repeat said perturbing and said storing to create at least one of (a) one or more feature vectors and (b) one or more quantity vectors.

9. A method as in claim 1, further comprising the production mode using the computer to apply the transformation function to the one or more feature vectors.

10. A method as in claim 9, further comprising the production mode using the computer to generate the one or more quantities of interest.

11. A method as in claim 10, further comprising the production mode using the computer to store the one or more quantities of interest.

12. A method as in claim 11, further comprising the production mode using the computer to process the quantities of interest to provide data for use in at least one of evaluation, diagnosis, prognosis, risk, treatment and treatment planning related to at least one of the production heart valve, production inflow tract, and production outflow tract.

13. A method as in claim 12 further comprising using said data to at least one of (1) guide clinical decision-making, (2) provide predictive information about disease progression, (3) provide information for risk stratification, (4) patient monitoring, (5) conducting sensitivity analyses, (6) evaluating an anatomic scenario, (7) evaluating a physiologic scenario, (8) evaluating a hemodynamic scenario, (9) estimating response to therapy, and (10) developing understanding of cardiac health.

14. A method as in claim 1 wherein said computer-implemented machine learning method includes a computed tomography device.

15. A method as in claim 1 wherein said computer-implemented machine learning method includes a magnetic resonance imaging device.

16. A method as in claim 1 wherein said computer-implemented machine learning method includes an ultrasound imaging device.

17. A method as in claim 1 wherein said machine learning system comprises a Doppler device.

18. A method as in claim 1 wherein said machine learning system comprises an electrophysiologic device.

19. A method as in claim 1 wherein said machine learning system comprises clinical instruments.

20. A method as in claim 1, further comprising the production mode using the computer to process the quantities of interest to provide data for use in at least one of evaluation, diagnosis, prognosis, risk, treatment and treatment planning related to at least one of the production heart valve, production inflow tract, and production outflow tract.

21. A method as in claim 1, further comprising the production mode using the computer to provide data for use in at least one of the construction and execution of a computer-based model of at least one of cardiac anatomy and physiology.

22. A method as in claim 1 further comprising:
(a) using a training mode of a machine learning system on the computer to train said computer and construct said transformation function based upon a plurality of images to predict said at least one of said unknown anatomical characteristic or said unknown physiological characteristic of at least one of said heart valve, said inflow tract or said outflow tract, using at least one of said known anatomical characteristic or said known physiological characteristic of the at least one heart valve, inflow tract or outflow tract;
(b) wherein said known anatomical characteristic or said known physiological characteristic of the at least one heart valve, inflow tract or outflow tract includes at least one of size, shape, and flow characteristics.

23. A method as in claim 22 wherein said transformation function is based upon at least one morphological simplification that exploits underlying geometric features.

24. A method as in claim 22 wherein said known anatomical characteristic or said known physiological characteristic of the at least one heart valve, inflow tract or outflow tract characterizes calcification.

25. A method as in claim 24 wherein said characterizes calcification includes location of calcification.

26. A method as in claim 24 wherein said characterizes calcification includes extent of calcification.

27. A method as in claim 24 wherein said characterizes calcification includes size of calcification.

28. A method as in claim 24 wherein said characterizes calcification includes degree of calcification.

29. A method as in claim 22, further comprising the training mode using the computer to store in said at least one of said one or more feature vectors which are representative of the at least one known anatomical characteristic or known physiological characteristic of the at least one heart valve, inflow tract or outflow tract.

30. A method as in claim 29, further comprising the training mode using the computer to calculate an approximate blood flow through the at least one heart valve, inflow tract or outflow tract.

31. A method as in claim 29, further comprising the training mode using the computer to store quantities associated with an approximate blood flow through the at least one heart valve, inflow tract or outflow tract in at least one or more feature vectors.

32. A method as in claim 29, further comprising the training mode using the computer to perturb the at least one known anatomical characteristic or known physiological characteristic of the at least one heart valve, inflow tract or outflow tract stored in at least one of said one or more feature vectors.

33. A method as in claim 32, further comprising the training mode using the computer to calculate a new approximate blood flow through the at least one heart valve, inflow tract or outflow tract with the perturbed at least one known anatomical characteristic or known physiological characteristic.

34. A method as in claim 33, further comprising the training mode using the computer to store quantities associated with a new approximate blood flow through the perturbed at least one heart valve, inflow tract or outflow tract.

35. A method as in claim 34, further comprising the training mode using the computer to repeat said perturbing and said storing to create at least one of feature vectors and quantity vectors.

36. A method as in claim 1, further comprising the production mode using the computer to generate the one or more quantities of interest that includes hemodynamic data.

37. A method as in claim 1, further comprising the production mode using the computer to generate the one or more quantities of interest that includes patient data.

38. A method as in claim 1, further comprising the production mode using the computer to generate the one or more quantities of interest that includes the location of the at least one production heart valve, production inflow tract or production outflow tract.

39. A method as in claim 1, further comprising the production mode using the computer to generate the one or more quantities of interest that includes qualitative information of the at least one production heart valve, production inflow tract or production outflow tract.

40. A method as in claim 1, further comprising the production mode using the computer to generate the one or more quantities of interest that includes quantitative information of the at least one production heart valve, production inflow tract or production outflow tract for use in evaluating valvular anatomy.

41. A method as in claim 1, further comprising the production mode using the computer to generate the one or more quantities of interest that includes quantitative information of the at least one production heart valve, production inflow tract or production outflow tract for use in evaluating physiology.

42. A method as in claim 1 wherein said transformation function characterizes discretized surface elements.

43. A method as in claim 1 wherein said transformation function characterizes discretized volume elements.

44. A method as in claim 1 wherein any of said unknown anatomic characteristic is an unknown geometrical anatomic characteristic.

45. A method as in claim 1 wherein said transformation is a multi-dimensional transformation function.

46. A method as in claim 1 wherein said transformation is a one-dimensional transformation function.

47. A method as in claim 1, further comprising using the computer to perform the following steps:
(a) receiving patient-specific data selected from the group consisting of anatomic data, physiologic data, and hemodynamic data;
(b) generating a digital model of the at least one production heart valve, production inflow tract or production outflow tract, based on the received data;
(c) discretizing the digital model;
(d) applying boundary conditions to at least one inflow portion and at least one outflow portion of the digital model; and
(e) initializing and solving mathematical equations of blood flow through the digital model.

48. A method as in claim 47, further comprising the computer storing quantities and parameters that characterize at least one of an anatomic state or a physiologic state of the digital model and the blood flow.

49. A method as in claim 47, further comprising the computer perturbing at least one of an anatomic parameter or a physiologic parameter that characterizes the digital model.

50. A method as in claim 49, further comprising the computer at least one of re-discretizing or re-solving the mathematical equations with the at least one anatomic parameter or physiologic parameter.

51. A method as in claim 50, further comprising the computer storing quantities and parameters that characterize at least one of the anatomic state or the physiologic state of the perturbed model and blood flow.

52. A method as in claim 1, further comprising the production mode using the computer to receive one or more feature vectors.

53. A method as in claim 52, further comprising the production mode using the computer to apply the transformation function to the feature vectors.

54. A method as in claim 53, further comprising the production mode using the computer to generate one or more quantities of interest.

55. A method as in claim 54, further comprising the production mode using the computer to process the quantities of interest to provide data for use in at least one of evaluation, diagnosis, prognosis, treatment or treatment planning related to a heart in which the at least one production heart valve, production inflow tract or production outflow tract resides.

* * * * *

UNITED STATES PATENT AND TRADEMARK OFFICE
CERTIFICATE OF CORRECTION

PATENT NO. : 10,762,442 B2  
APPLICATION NO. : 15/588317  
DATED : September 1, 2020  
INVENTOR(S) : Michael A. Singer Page 1 of 2

It is certified that error appears in the above-identified patent and that said Letters Patent is hereby corrected as shown below:

In the Claims

Column 13, Line 58 in Claim 1: After "one" insert --of a--;
Column 13, Line 58 in Claim 1: After "valve," insert --an--;
Column 13, Line 58 in Claim 1: After "tract or" insert --an--;

Column 13, Line 66 in Claim 1: After "one" insert --of a--;

Column 13, Line 67 in Claim 1: After "valve," insert --a--;
Column 13, Line 67 in Claim 1: After "tract or" insert --a--;

Column 14, Line 2 in Claim 1: After "or patient" insert --specific patient--;

Column 14, Line 4 in Claim 1: Before "production" insert --of a--;
Column 14, Line 4 in Claim 1: After "valve," insert --a--;
Column 14, Line 4 in Claim 1: After "tract or" insert --a--;

Column 14, Line 11 in Claim 2: Delete "at";

Column 14, Line 12 in Claim 2: Delete "least";

Column 14, Line 13 in Claim 2: After "one patient" insert --specific patient--;
Column 14, Line 13 in Claim 2: After "or patient" insert --specific patient--;

Column 14, Line 14 in Claim 2: After "one" insert --of a--;

Column 14, Line 15 in Claim 2: After "valve," insert --a--;
Column 14, Line 15 in Claim 2: After "tract or" insert --a--;

Column 14, Line 27 in Claim 5: After "one patient" insert --specific patient--;

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,762,442 B2

Column 14, Line 28 in Claim 5: After "or patient" insert --specific patient--;

Column 14, Line 30 in Claim 5: Delete "the";

Column 14, Line 36 in Claim 6: Delete "known" and replace with --of--;
Column 14, Line 36 in Claim 6: After the first occurrence of "patient" insert --specific patient known--;
Column 14, Line 36 in Claim 6: After "or patient" insert --specific patient--;

Column 14, Line 57 in Claim 12: After "process the" insert --one or more--;

Column 14, Line 60 in Claim 12: After "related to" insert --the--;
Column 14, Line 60 in Claim 12: After "one of" delete "the";

Column 15, Line 21 in Claim 20: After "process the" insert --one or more--;

Column 15, Line 24 in Claim 20: After "related to" insert --the--;
Column 15, Line 24 in Claim 20: After "one of" delete "the";

Column 16, Line 39 in Claim 38: Replace "includes the" with --includes a--;

Column 16, Line 64 in Claim 44: Replace "anatomic" with --anatomical--;

Column 16, Line 66 in Claim 45: After "transformation" insert --function--;

Column 17, Line 1 in Claim 46: After "transformation" insert --function--;

Column 17, Line 8 in Claim 47: After "one" insert --of--;

Column 18, Line 10 in Claim 52: After "mode" insert --of the machine learning system on the computer--;
Column 18, Line 10 in Claim 52: After "receive" insert --the--;

Column 18, Line 13 in Claim 53: After "using" insert --one or more--;

Column 18, Line 16 in Claim 53: After "generate" insert --the--; and

Column 18, Line 19 in Claim 55: After "the" insert --one or more--.